United States Patent [19]
Mitchell

[11] 3,962,037
[45] June 8, 1976

[54] COMPOSITION FOR STABILIZING AN ENZYME-CONTAINING REAGENT

[75] Inventor: Robert Jerry Mitchell, Elkhart, Ind.

[73] Assignee: Miles Laboratories, Inc., Elkhart, Ind.

[22] Filed: Jan. 30, 1975

[21] Appl. No.: 545,733

[52] U.S. Cl. .................................. 195/63; 195/68
[51] Int. Cl.² ........................................... C12K 1/00
[58] Field of Search ............... 195/63, 68, 99, 103.5

[56] References Cited
UNITED STATES PATENTS

| | | | |
|---|---|---|---|
| 2,908,614 | 10/1959 | Muggleton et al. | 195/68 UX |
| 3,448,009 | 6/1969 | Roberts | 195/63 |
| 3,527,674 | 9/1970 | Deutsch | 195/63 X |

FOREIGN PATENTS OR APPLICATIONS 1,286,095   8/1972   United Kingdom

Primary Examiner—A. Louis Monacell
Assistant Examiner—Robert J. Warden

[57] ABSTRACT

A composition for stabilizing an enzyme-containing reagent, which composition comprises dextran and Cleland's reagent.

8 Claims, No Drawings

COMPOSITION FOR STABILIZING AN ENZYME-CONTAINING REAGENT

BACKGROUND OF THE INVENTION

This invention relates to a composition for stabilizing an enzyme-containing reagent.

It is known in the prior art that one way to prolong the useful life of reagents which include enzymes is to supply such reagents in a dry form. It is also known that when such dry reagents are made up into aqueous liquid systems they rapidly loose their activity, such that after a relatively short time they can no longer be used. Such loss of activity often occurs in less than 24 hours, even when the reagent is refrigerated. As a result, a considerable amount of time must be spent in preparing fresh liquid reagent systems.

SUMMARY OF THE INVENTION

This invention is embodied in a novel composition for stabilizing an enzyme-containing reagent, which composition is particularly effective in stabilizing such reagent when the latter is in an aqueous liquid system. This composition consists essentially of dextran and Cleland's reagent. Such composition may be in dry form and incorporated with reagent components also in dry form, or it may be added separately to a liquid reagent system to be stabilized.

It is an object of this invention to provide a composition which substantially prolongs the useful life of an enzyme-containing reagent when the latter is in a liquid system.

It is a further object of this invention to provide a composition which by prolonging the useful life of a reagent, obviates the waste of such reagent heretofore caused by loss of activity.

DESCRIPTION OF THE INVENTION

It has unexpectedly been found that a composition consisting essentially of dextran and Cleland's reagent, when included in or with an enzyme-containing reagent, substantially prolongs the useful life of such reagent when the latter is in a liquid system, and particularly when it is in an aqueous system. Accordingly, the composition of this invention permits more efficient use of enzyme-containing reagents and laboratory personnel than was previously possible.

In the following description all references to an aqueous system shall mean a combination of a reagent and an aqueous medium therefor.

The dextran used in the stabilizing composition of this invention is selected from one having a molecular weight greater than about 50,000. Preferably the dextran selected has a molecular weight of about 500,000. Such materials are well known in their own right and are readily available to one skilled in the art. Beneficially at least 0.1 percent by weight of dextran is present based upon the combined weight of the stabilizing composition and the aqueous system. A preferred concentration of dextran is about 1 percent.

The Cleland's reagent is advantageously present in an amount between 0.5 mM. and 3 mM. in the aqueous system. It is to be recognized that Cleland's reagent is also known as dithiothreitol or its isomer dithioerythritol which may be used alone or in combination in the composition. Preferably this material is included in an amount of about 1 mM. in the aqueous system.

In the following example the composition of this invention is incorporated with an enzyme-containing reagent for use in measuring the amount of glycerol in an aqueous fluid. This example demonstrates the capability of this stabilizing composition to maintain the activity of the reagent in the aqueous system.

EXAMPLE

In this Example the following abbreviations are used:
ATP = adenosine — 5' — triphosphate
GK = glycerol kinase
GP = α — glycerol phosphate
ADP = adenosine — 5' — diphosphate
PEP = phosphoenolpyruvate
PK = pyruvate kinase
$NADH_2$ = nicotinamide adenine dinucleotide (reduced)
NAD = nicotinamide adenine dinucleotide (oxidized)

Olive oil, which is substantially pure glycerides, was saponified to glycerol and the glycerol was measured with aqueous liquid reagent systems which did and did not include the composition of this invention at predetermined times following the preparation thereof.

For the saponification, 0.5 ml. of a solution of 800 mg. of olive oil in 100 ml. ethanol was mixed with 2.2 ml. of 0.5N KOH in 67.3% ethanol. The mixture was saponified by being maintained at 37°C. for about 12 minutes. To the saponified mixture, 5.3 ml. of a 0.112 M $MgSO_4$ solution was added and mixed therewith. This combination was filtered and the filtrate retained.

The following aqueous systems were prepared:
System A
ATP 0.6 mg. (disodium salt)
PEP 1.0 mg. (tricyclohexyl ammonium salt)
PK (5) I.U. (International Units)
*GK (1.0) IU
0.025 M Tris-HCl buffer pH 7.6, 2.7 ml.

*The G.K. was derived from an E. coli microbial source.

System B
This system was the same as System A except that the G.K. was derived from a C. mycoderma microbial source.

Systems C & D
These systems were the same as A and B except that 1 mM dithiothreitol and 270 mg. dextran (500,000 molecular weight) was added to each system respectively.

The glycerol was measured by adding to 1.3 ml. of the filtrate, 2.7 ml. of the system being evaluated. Such combination was mixed and allowed to stand for 12 minutes at 37°C. To this mixture, 1 ml. of a color reagent, 0.05% 2,4-dinitrophenylhydrazine (DNPH) in 1N HCl, was added, mixed well and allowed to stand for 5 minutes. The pH of the mixture with the color reagent was adjusted to a high basic pH by mixing therewith 0.3 ml. of an 8N NaOH solution. This final mixture was allowed to stand for 5 minutes at room temperature, about 22°C., after which absorbance was measured at 550 nm. with a colorimeter.

The general reaction sequence which resulted in a colored product which absorbed light at 550 nm. is as follows:

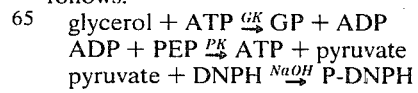

the P-DNPH was pyruvate diphenylhydrazone which is brownish in a basic pH.

The respective systems were observed for loss of activity over a 6 day period of storage in suitable containers at 5°C. Loss of activity was based upon the difference between the absorbance observed with the freshly prepared system and that observed with the same system after storage. A loss of more than 10 percent activity by a system was considered unacceptable, since results obtained with such system would be clearly outside acceptable limits of variation. A maximum storage period of 6 days was used, since such systems should not be prepared in quantities which cannot be used within such a period.

It was observed that System A had more than about a 90 percent loss of activity after 6 days of storage. For System B about a 30 percent loss of activity was observed after 6 days of storage. For System C it was observed that there was less than about a 1 percent loss of activity after 6 days of storage. For System D it was observed that there was less than about a 10 percent loss of activity after 6 days of storage.

These observed results demonstrated that liquid enzyme-containing reagent systems including the composition of this invention retained useful activity over the desired period of storage, whereas similar systems which did not include the composition of this invention did not retain useful activity over such period.

What is claimed is:

1. A stabilized enzyme-containing reagent composition comprising a mixture of glycerol kinase and pyruvate kinase and a stabilizing composition consisting essentially of dextran and Cleland's reagent.

2. A composition according to claim 1 wherein said dextran has a molecular weight of at least 50,000.

3. A composition according to claim 1 wherein said Cleland's reagent is dithiothreitol, dithioerythritol or combinations thereof.

4. The composition of claim 1 wherein the constituents thereof are in dry form.

5. The composition of claim 1 in a liquid medium.

6. The composition of claim 5 wherein the liquid medium is aqueous.

7. The composition of claim 6 wherein the dextran is present in an amount of at least 0.1 percent by weight of the total weight of the system comprising the enzyme-containing reagent, dextran, Cleland's reagent and aqueous medium.

8. The composition of claim 6 wherein the Cleland's reagent is present in an amount between 0.5 mM. and 3 mM.

* * * * *